United States Patent [19]
Kaiser et al.

[11] 3,985,887
[45] Oct. 12, 1976

[54] 3-SUBSTITUTED-4-HYDROXYPHENYL-2-PIPERIDYLCARBINOLS AS β-ADRENERGIC STIMULANTS

[75] Inventors: Carl Kaiser, Haddon Heights; Joe R. Wardell, Jr., Willingboro, both of N.J.

[73] Assignee: SmithKline Corporation, Philadelphia, Pa.

[22] Filed: June 11, 1975

[21] Appl. No.: 585,897

Related U.S. Application Data

[62] Division of Ser. No. 408,147, Oct. 19, 1973, Pat. No. 3,910,933.

[52] U.S. Cl. .............................................. 424/267
[51] Int. Cl.² ...................................... A61K 31/445
[58] Field of Search ..................................... 424/267

[56] References Cited
UNITED STATES PATENTS

| | | | |
|---|---|---|---|
| 2,976,291 | 3/1961 | Jacob et al. | 424/267 |
| 3,574,741 | 4/1971 | Gould et al. | 424/267 |
| 3,655,676 | 4/1972 | Kaiser et al. | 424/267 |
| 3,661,917 | 5/1972 | Kaiser et al. | 424/267 |
| 3,711,545 | 1/1973 | Kaiser et al. | 424/267 |

OTHER PUBLICATIONS

Larsen et al, J. Med. Chem. 10:462–472 (1967) RS1J5.
Kaiser Chemical Abstracts 77:151996v (1972).
Kaiser et al, Chemical Abstracts 75:35755a (1971).
Kaiser et al. Chemical Abstracts 75:140529c (1971).

*Primary Examiner*—Norman A. Drezin
*Attorney, Agent, or Firm*—Stuart R. Suter; William H. Edgerton; Alan D. Lourie

[57] ABSTRACT

3-Substituted-3-hydroxyphenyl-2-piperidylcarbinols are prepared. These compounds are β-adrenergic stimulants and are useful in particular as bronchodilators.

10 Claims, No Drawings

3-SUBSTITUTED-4-HYDROXYPHENYL-2-PIPERIDYLCARBINOLS AS β-ADRENERGIC STIMULANTS

This is a div. of appl. Ser. No. 408,147 filed Oct. 19, 1973 now U.S. Pat. No. 3,910,933.

This invention relates to novel 3-substituted-4-hydroxyphenyl-2-piperidylcarbinols which have useful pharmacodynamic activity. More specifically the compounds of this invention have utility as β-adrenergic stimulants with relatively greater activity on respiratory smooth muscle than on cardiac muscle. Therefore, the compounds have direct bronchodilator action with minimal cardiac stimulation.

The compounds of this invention are represented by the following structural formula:

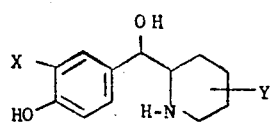

wherein:
X is $R_2NCONH$, $RCONH$, $R_2N$, $R'OCONH$, $R_2NSO_2NH$, or $R'SO_2CH_2$;
each R is hydrogen or $C_1$–$C_3$ alkyl;
R' is $C_1$–$C_3$ alkyl; and
Y is hydrogen or $C_1$–$C_6$ alkyl.

Advantageous compounds of the above formula are those where Y is hydrogen, R is hydrogen, methyl or ethyl, and R' is methyl or ethyl.

The compounds of this invention may be used in the form of a pharmaceutically acceptable acid addition salt having the utility of the free base. Such salts, prepared by methods well known to the art, are formed with both inorganic or organic acids, for example: maleic, fumaric, benzoic, ascorbic, pamoic, succinic, bis-methylenesalicyclic, methanesulfonic, ethanedisulfonic, acetic, oxalic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids.

The compounds of this invention may be present as diastereoisomers and are designated as erythro and threo isomers which may be resolved as d, l optical isomers. Unless otherwise specified in the description and accompanying claims, it is intended to include all isomers, whether separated or mixtures thereof.

The compounds of this invention are prepared by a sequence of reactions, one such sequence of reactions is as follows:

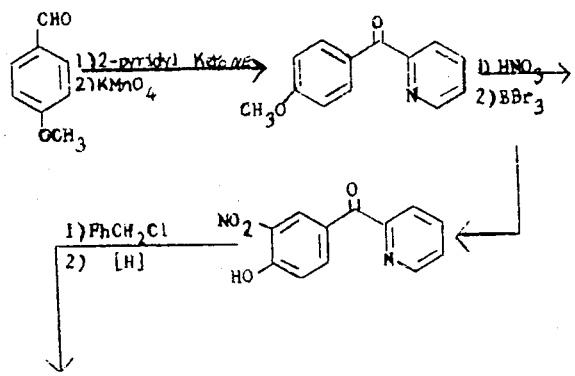

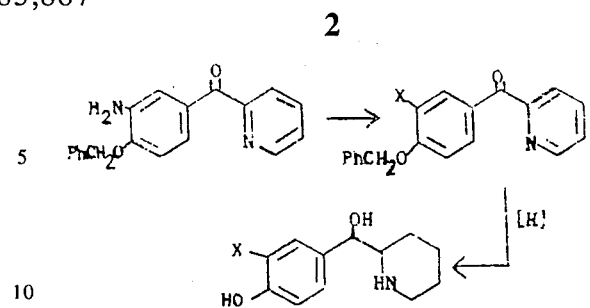

General methods for the preparation of phenyl pyridyl ketones are known in the art (Sankey and Whiting, J. Heterocyclic Chem., 9, 1049 (1972). These methods include reacting an arylaldehyde, for example anisylaldehyde, with a picolinic acid or pyridyl lithium to give a carbinol which is oxidized to the ketone. In addition, a Friedel-Craft reaction of anisole and a picolinic acid chloride also gives the ketone. The 4-methoxyphenyl pyridyl ketones are nitrated to give 4-methoxy-3-nitrophenyl pyridyl ketone. Cleavage of the ether group followed by reaction with benzyl chloride and then chemical reduction gives 3-amino-4-benzyloxyphenyl 2-pyridyl ketone. This compound is hydrogenated or the amino group may be reacted with appropriate reagents prior to hydrogenation to give compounds of this invention. The above mentioned appropriate reagents include alkylation and acylation reagents, such as anhydrides, carboxylic acid chlorides, sulfamyl chlorides, alkyl formates and alkyl halides. When X is ureido the amino group is reacted with cyanate ion, an alkyl cyanate or a dialkylcarbamoyl chloride.

Compounds where X is $R'SO_2CH_2$ are prepared by a sequence of reactions such as the following.

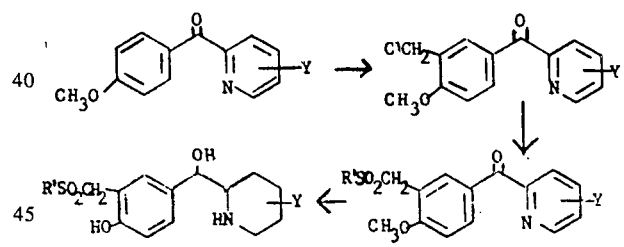

The phenyl pyridyl ketone is treated with formaldehyde and hydrochloric acid in the presence of zinc chloride to give the chloromethyl compound. Treatment of this compound with alkyl magnesium sulfinates followed by ether cleavage and reduction gives the desired carbinols.

The compounds of this invention are β-adrenergic stimulants which have direct bronchodilator activity with minimal cardiac stimulation. This selective β-stimulant activity is determined by two standard in vitro pharmacological test systems: (1) effect on spontaneous tone of guinea pig tracheal chain preparation as a measure of β-stimulant (direct relaxant) effect on airway smooth muscle, and (2) effect on spontaneously beating right atria of the guinea pig as a measure of β-stimulant effect on cardiac muscle. Compounds that show selective bronchodilating properties, as the compounds of this invention do, are active in test (1) at a dose lower than is required in test (2) thereby resulting in a positive separation ratio. Results of test (1) are reported as the dose which produces 50% of the maximum possible relaxation ($ED_{50}$). Test (2) results are reported as the dose which produces 25% of the maximum possible increase in atrial contraction rate ($ED_{25}$).

A preferred compound of this invention is α-(3-amino-4-hydroxyphenyl)-2-piperidylcarbinol which has an $ED_{50}$ of 0.12 mcg/ml and an $ED_{25}$ of 4.4 mcg/ml. Another preferred compound, α-(4-hydroxy-3-methanesulfonylmethylphenyl)-2-piperidylcarbinol, has an $ED_{50}$ of 0.14 mcg/ml and an $ED_{25}$ of 1.1 mcg/ml. In addition, α-(4-hydroxy-3-ureidophenyl)-2-piperidylcarbinol has an $ED_{50}$ of 0.83 mcg/ml and an $ED_{25}$ of 9.4 mcg/ml.

The compounds of this invention may be administered orally or parenterally in conventional dosage unit forms such as tablets, capsules, injectables or the like, by incorporating the appropriate dose of a compound of formula I, with carriers according to accepted pharmaceutical practices. Preferably a compound or an acid addition salt thereof is administered orally to an animal organism in a tablet or capsule comprising an amount sufficient to produce β-adrenergic stimulant activity. Each dosage unit will contain the active medicament in an amount of about 25 mg to about 50 mg. Advantageously, equal doses will be administered 3 to 4 times daily with the daily dosage regimen being about 75 mg to about 200 mg.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly the carrier or diluent can include any time delay material well known to the art, such as glyceryl monostearate or glyceryl distearate alone or with a wax.

A wide variety of pharmaceutical forms can be employed. Thus, if a solid carrier is used the preparation can be tableted, placed in a hard gelatin capsule in powder or pellet form, or in the form of a troche or lozenge. The amount of solid carrier will vary widely but preferably will be about 25 mg to about 1 g. If a liquid carrier is used, the preparation will be in the form of a syrup, emulsion, soft gelatin capsule, sterile injectable liquid such as an ampule, or an aqueous or nonaqueous liquid suspension. Of particular applicability for intranasal administration is an aerosol dispensing system wherein the active medicament is incorporated with Freon or other inert propellant in an aerosol container. Such an aerosol system will deliver a metered dose of about 250 mcg to about 500 mcg, administered once or twice at a time as needed. Also useful for this purpose is a liquid formulation in a plastic squeeze bottle.

The following example illustrates the preparation of specific compounds having β-adrenergic stimulant activity and should not be construed as a limitation of the invention.

EXAMPLE 1

To one mole of butyl lithium (15% in hexane) at −40° C under nitrogen is added gradually a solution of 142 g (0.9 mol) of 2-bromopyridine in 340 ml. of ether, maintaining the temperature below −40° C. After stirring for 15 minutes at this temperature, a solution of 122 g (0.9 mol) of 4-methoxybenzaldehyde in 250 ml of ether is added, with the temperature below −15° C. The reaction mixture is stirred for 40 minutes at this temperature, quenched in 1.5 l ice water. The solid is filtered and washed with cold ether to give 4-methoxyphenyl-2-pyridylcarbinol, m.p. 126°–130° C.

To a stirred mixture of 76.5 g (0.36 mol) of the above pyridylcarbinol in 900 ml water at 70° is added in portions 70.5 g (0.446 mol) of potassium permanganate. The reaction temperature is maintained at 90°–100° C. for 1 hour, the heat is withdrawn and excess ethyl acetate is added gradually. The mixture is filtered and the filter cake is washed with hot ethyl acetate. The combined ethyl acetate solution is washed with water, dried and evaporated in vacuo to yield 4-methoxyphenyl 2-pyridyl ketone, mp 96°–98° C.

To a stirring mixture of 3 ml (48.3 mmol) 71% $HNO_3$ and 200 ml $H_2SO_4$ at −15° C was gradually added 10.0 g (46.9 mmol) of the above ketone. The reaction is maintained at −5° to −8° for 30 minutes, quenched on ice, and neutralized with solid $Na_2CO_3$. The solid 4-methoxy-3-nitrophenyl 2-pyridyl ketone is collected, mp 115°–118° C.

To a cold solution of 9.4 g (36.4 mmol) of the nitroketone in 40 ml methylene chloride is added slowly with stirring 9.4 ml (25 g) $BBr_3$. The reaction is stirred without cooling for 1 hour, evaporated in vacuo, and quenched in water. The solid, 4-hydroxy-3-nitrophenyl 2-pyridyl ketone, is collected, mp 155°–60° C.

The above phenol (23.2 g, 0.096 mol) is added gradually to a suspension of sodium hydride (2.5 g, 0.11 mol) in 120 ml dimethyl sulfoxide. When hydrogen evolution subsides, benzyl chloride (13.3 g, 0.105 mol) is added and the mixture is heated to 100° for 4 hours. The reaction is quenched in water and extracted with ether. The extracts are washed with water, dried, and evaporated to 4-benzyloxy-3-nitrophenyl 2-pyridyl ketone which is triturated with ethanol.

To a refluxing mixture of 19.2 g (0.058 mol) of the above nitrophenyl compound and 2 teaspoonsful of Raney nickel in 200 ml ethanol is added over a 15-minute period a solution of 9.6 g of 99% hydrazine hydrate in 30 ml ethanol. The reaction is refluxed 1 hour, cooled, and evaporated to a residue which is dissolved in ether. The ether solution is treated with decolorizing carbon and evaporated to give 3-amino-4-benzyloxyphenyl 2-pyridyl ketone as an oil, 14.2 g (86%).

EXAMPLE 2

A solution of 10.0 g (32.8 mmol) of 3-amino-4-benzyloxyphenyl 2-pyridyl ketone in 40 ml of 83% acetic acid in water is treated with 6.4 g (0.1 mol) sodium cyanate. The reaction is stirred at room temperature for 1 hour and then at 100° for 15 minutes. Additional sodium cyanate (2–4 g) is added and the solution is stirred until room temperature is obtained. The reaction is quenched with water, and adjusted to pH 10 with 40% NaOH. The product, 4-benzyloxy-3-ureidophenyl 2-pyridyl ketone is collected, mp 183°–5° C.

A solution of 1.73 g (5 mmol) of the above product in 15 ml concentrated HCl and 15 ml glacial acetic acid is heated on a steam bath for 1 hour, 10 ml concentrated HCl is added and heating is continued for 1 hour. The solution is concentrated in vacuo and the solid residue is recrystallized from methanol-ether. The solid is hydrogenated in 80 ml methanol and 20 ml water with 0.3 g $PtO_2$ at 60 psi until hydrogen uptake stops. After filtration, the solution is evaporated and the residue is stripped with ether and triturated with acetone to give α-(4-hydroxy-3-ureidophenyl)-2-piperidylcarbinol hydrochloride.

Treatment of 3-amino-4-benzyloxyphenyl 2-pyridyl ketone with an equimolar amount of methyl isocyanate in benzene followed by debenzylation and hydrogenation as described in the above procedure gives α-[4-hydroxy-3-(3-methylureido)phenyl]-2-piperidylcarbinol.

EXAMPLE 3

To an ice-cooled solution of 20.0 g (77.5 mmol) 4-methoxy-3-nitrophenyl 2-pyridyl ketone in 100 ml methylene chloride is added 20 ml BBr$_3$ over a 10-minute period. Solution is then stirred at room temperature for 1 hour. The reaction is evaporated in vacuo at <50°, and excess methanol is gradually added to the residue and the resulting solution is evaporated. The methanol treatment is repeated. The residue is treated with water and NaHCO$_3$; the solid 4-hydroxy-3-nitrophenyl 2-pyridyl ketone hydrobromide is collected, mp 157°–9°.

A mixture of 0.5 g of the above product and 0.1 g PtO$_2$ in 50 ml methanol is hydrogenated at 50 psi for 1 hour. The catalyst is removed and 0.1 g 10% Pd on carbon is added and the hydrogenation is repeated. After filtration the solvent is evaporated and the residue is boiled with ethyl acetate and filtered to give α-(3-amino-4-hydroxyphenyl)-2-piperidylcarbinol hydrobromide.

EXAMPLE 4

A mixture of 10.0 g (32.8 mmol) of 3-amino-4-benzyloxyphenyl 2-pyridyl ketone and 40 ml of acetic anhydride is heated on a steam bath for 1 hour. The reaction is concentrated in vacuo to give a residue which is suspended in water and made basic with 10% NaOH. The aqueous phase is extracted with ether and the dried extracts are evaporated to give 3-acetamido-4-benzyloxyphenyl 2-pyridyl ketone.

The ketone is debenzylated and reduced according to the procedure in Example 3 using PtO$_2$ as catalyst to yield α-(3-acetamido-4-hydroxyphenyl)-2-piperidylcarbinol.

EXAMPLE 5

A mixture of 10.0 g (32.8 mmol) of 3-amino-4-benzyloxyphenyl 2-pyridyl ketone and 200 ml of ethyl formate is refluxed with stirring for 24 hours. The reaction mixture is evaporated and the residue is dissolved in methylene chloride, then is washed with dilute HCl and saturated saline solution. The dried organic phase is evaporated to give 4-benzyloxy-3-formamidophenyl 2-pyridyl ketone.

Debenzylation and reduction of this product by hydrogenation over PtO$_2$ according to the procedure of Example 3 gives α-(3-formamido-4-hydroxyphenyl)-2-piperidylcarbinol.

EXAMPLE 6

A solution of 4.7 g (32.8 mmol) of dimethylsulfamyl chloride in 5 ml of dry pyridine is added to 5.0 g (16.4 mmol) of 3-amino-4-benzyloxyphenyl 2-pyridyl ketone in 100 ml of dry pyridine at 0°–10° C. The reaction mixture is stirred in the cold overnight and then poured in water and extracted with ether. The ether extract is washed with water and extracted with dilute aqueous KOH. This basic extract is washed with ether, acidified with hydrochloric acid and extracted with methylene chloride. The dried organic extract is evaporated in vacuo to give 4-benzyloxy-3-dimethylsulfamoylaminophenyl 2-pyridyl ketone. Hydrogenation over PcO$_2$ according to the procedure of Example 3 gives α-(4-hydroxy-3-dimethylsulfamoylaminophenyl)-2-piperidylcarbinol.

EXAMPLE 7

To a stirred solution of 3.8 g (32.8 mmol) of sulfamyl chloride in 60 ml of dry benzene at 10° C is added, in small portions, 10.0 g (32.8 mmol) of 3-amino-4-benzyloxyphenyl 2-pyridyl ketone. The reaction mixture is stirred at 10°–20° C for 30 minutes and then extracted with 5% sodium hydroxide. Addition of hydrochloric acid to the basic extracts precipitates the product, 4-benzyloxy-3-sulfamoylaminophenyl 2-pyridyl ketone, which is hydrogenated according to the procedure of Example 3 to give α-(4-hydroxy-3-sulfamoylaminophenyl)-2-piperidylcarbinol.

EXAMPLE 8

An anhydrous benzene solution of 3-acetamido-4-benzyloxyphenyl 2-pyridyl ketone is heated at reflux with sodium until a suspension is formed. To this suspension is added sulfuryl chloride in benzene and the resulting mixture is filtered to remove sodium chloride. The filtrate is evaporated to give 4-benzyloxy-3-(N-chlorosulfonylacetamido)phenyl 2-pyridyl ketone.

An equimolar mixture of the above product and methylamine is heated in anhydrous benzene at 50° C for 4 hours, cooled and filtered. The filtrate is treated with dilute HCl and the organic phase is separated and extracted with naOH. NAOH. The basic extract is acidified to give 4-benzyloxy-3-methylsulfamoylaminophenyl 2-pyridyl ketone which is hydrogenated over PtO$_2$ by the procedure of Example 3 to give α-(4-hydroxy-3-methylsulfamoylaminophenyl)-2-piperidylcarbinol.

EXAMPLE 9

A stirred solution of 40 g (0.41 mol) of phosgene in 150 ml of toluene is held at 25° C while a mixture of (52.5 mmol) of 3-amino-4-benzyloxyphenyl 2-pyridyl ketone and 300 ml of toluene is added slowly. The mixture is refluxed for 30 minutes and then is concentrated to give 4-benzyloxy-3-isocyanatophenyl 2-pyridyl ketone.

A solution of 10 g of the isocyanate in 150 ml of ethanol is refluxed for 2 hours and then concentrated to give 4-benzyloxy-3-carbethoxyaminophenyl 2-pyridyl ketone.

Hydrogenation over PtO$_2$ as described in Example 3 gives α-(3-carbethoxyamino-4-hydroxyphenyl)-2-piperidylcarbinol.

Substitution of methanol or isopropanol for ethanol in the above procedure gives as final products α-(3-carbomethoxyamino-4-hydroxyphenyl)-2-piperidylcarbinol and α-(3-carboisopropoxyamino-4-hydroxyphenyl)-2-piperidylcarbinol.

EXAMPLE 10

Into a mixture of 10.0 g (47 mmol) of 4-methoxyphenyl 2-pyridyl ketone, 3.7 g of formaldehyde, 6.89 g of anhydrous ZnCl$_2$, and 25 ml of acetic acid is passed gaseous HCl. The reaction is quenched in water, neutralized with solid NaHCO$_3$ and extracted with ether. The dried extracts are evaporated to give 3-chloromethyl-4-methoxyphenyl 2-pyridyl ketone, mp 92°–4° C.

To a slurry of 2.61 g (0.01 mol) of the above product in methanol is added a solution of 1.2 g (5.5 mmol) of methyl magnesium sulfinate in hot water. The mixture is refluxed for 4 hours and then poured into cold water. The aqueous solution is extracted with chloroform. The dried extracts are evaporated and the residue triturated with ether to give 3-methanesulfonylmethyl-4-methoxyphenyl 2-pyridyl ketone.

A solution of 0.75 g (2.45 mmol) of the above product in 25 ml of 48% HBr is refluxed for 4 hours and then concentrated to a solid residue which is recrystallized from methanol-ether to give 4-hydroxy-3-methanesulfonylmethylphenyl 2-pyridyl ketone hydrobromide, mp 230°–2° C.

A solution of 5 g of the above hydrobromide in 70% aqueous ethanol is hydrogenated over 0.2 g of $PtO_2$. The solvent is removed and the resultant oil is treated with methanol-ether to give α-(4-hydroxy-3-methanesulfonylmethylphenyl)-2-piperidylcarbinol hydrobromide, mp 224°–5° C.

EXAMPLE 11

To a boiling solution of 50 g of 4-methoxybenzaldehyde in 50 ml of p-cymeme is added 11.2 g of 6-methylpicolinic acid. After heating for 3 hours, the reaction is cooled and extracted with 2N HCl. The acidic extracts are washed with ether, made basic with ammonia and extracted with ether. Concentration of the dried ether extracts gives 4-methoxyphenyl-(6-methyl-2-pyridyl)-carbinol.

A suspension of 10 g of the above carbinol in 200 ml of water is maintained at 20° C while 5 g of $KMnO_4$ is added portionwise as the color is discharged. Excess reagent is destroyed by the addition of ethanol. The $MnO_2$ is removed by filtration and washed with boiling acetone. The filtrate is concentrated until the product, 4-methoxyphenyl (6-methyl-2-pyridyl) ketone precipitates.

Substitution of 5-n-butylpicolinic acid in the above procedure for 6-methylpicolinic acid gives 4-methoxyphenyl-(5-n-butyl-2-pyridyl)carbinol which is oxidized in the same manner to 4-methoxyphenyl (5-n-butyl-2-pyridyl) ketone.

EXAMPLE 12

4-Methoxyphenyl (6-methyl-2-pyridyl) ketone and 4-methoxyphenyl (5-n-butyl-2-pyridyl) ketone are nitrated, cleaved with $BBr_3$, treated with benzyl chloride and reduced according to the procedures of Example 1 to give 3-amino-4-benzyloxyphenyl (6-methyl-2-pyridyl) ketone and 3-amino-4-benzyloxyphenyl (5-n-butyl-2-pyridyl) ketone. These compounds are substituted for 3-amino-4-benzyloxyphenyl 2-pyridyl ketone in Example 2 to give α-(4-hydroxy-3-ureidophenyl)-6-methyl-2-piperidylcarbinol hydrochloride and α-(4-hydroxy-3-ureidophenyl)-5-n-butyl-2-piperidylcarbinol hydrochloride. The analogous methylureido compounds are prepared as described in Example 2.

EXAMPLE 13

When 4-methoxy-3-nitrophenyl (6-methyl-2-pyridyl) ketone or 4-methoxy-3-nitrophenyl (5-n-butyl-2-pyridyl) ketone are cleaved and reduced by the procedure of Example 3, α-(3-amino-4-hydroxyphenyl)-6-methyl-2-piperidylcarbinol hydrobromide and α-(3-amino-4-hydroxyphenyl)-5-n-butyl-2-piperidylcarbinol hydrobromide are obtained.

EXAMPLE 14

Substitution of 3-amino-4-benzyloxyphenyl (6-methyl-2-pyridyl) ketone or 3-amino-4-benzyloxyphenyl (5-n-butyl-2-pyridyl) ketone for 3-amino-4-benzyloxyphenyl 2-pyridyl ketone in Examples 4,5,6,7,8 and 9 gives the appropriate following products:

α-(3-acetamido-4-hydroxyphenyl)-6-methyl-2-piperidylcarbinol
α-(3-acetamido-4-hydroxyphenyl)-5-n-butyl-2-piperidylcarbinol
α-(3-formamido-4-hydroxyphenyl)-6-methyl-2-piperidylcarbinol
α-(3-formamido-4-hydroxyphenyl)-5-n-butyl-2-piperidylcarbinol
α-(4-hydroxy-3-dimethysulfamoylaminophenyl)-6-methyl-2-piperidylcarbinol
α-(4-hydroxy-3-dimethylsulfamoylaminophenyl)-5-n-butyl-2-piperidylcarbinol
α-(4-hydroxy-3-sulfamoylaminophenyl)-6-methyl-2-piperidylcarbinol
α-(4-hydroxy-3-sulfamoylaminophenyl)-5-n-butyl-2-piperidylcarbinol
α-(4-hydroxy-3-methylsulfamoylaminophenyl)-6-methyl-2-piperidylcarbinol
α-(4-hydroxy-3-methylsulfamoylaminophenyl)-5-n-butyl-2-piperidylcarbinol
α-(3-carbethoxyamino-4-hydroxyphenyl)-6-methyl-2-piperidylcarbinol
α-(3-carbethoxyamino-4-hydroxyphenyl)-5-n-butyl-2-piperidylcarbinol
α-(3-carbomethoxyamino-4-hydroxyphenyl)-6-methyl-2-piperidylcarbinol
α-(3-carbomethoxyamino-4-hydroxyphenyl)-5-n-butyl-2-piperidylcarbinol
α-(3-carboisopropoxyamino-4-hydroxyphenyl)-6-methyl-2-piperidylcarbinol
α-(3-carboisopropoxyamino-4-hydroxypheny)-5-n-butyl-2-piperidylcarbinol

EXAMPLE 15

The preparation of α-(4-hydroxy-3-methanesulfonylmethylphenyl)-6-methyl-2-piperidylcarbinol hydrobromide and α-(4-hydroxy-3-methanesulfonylmethylphenyl)-5-n-butyl-2-piperidylcarbinol hydrobromide is effected by the substitution of 4-methoxyphenyl 6-methyl-2-pyridyl ketone and 4-methoxyphenyl 5-n-butyl-2-pyridyl ketone for 4-methoxyphenyl 2-pyridyl ketone in the procedure of Example 10.

EXAMPLE 16

| Ingredients | Mg/Tablet | |
| --- | --- | --- |
| α-(4-Hydroxy-3-ureidophenyl)-2-piperidylcarbinol hydrochloride | 1.13* | 11.3** |
| Lactose | 63 | 100 |
| Starch | 4.9 | 9 |
| Magnesium stearate | 0.35 | 0.6 |

*Equivalent to 1 mg of the free base
**Equivalent to 10 mg of the free base

A granulation of the above ingredients is compressed into tablets using 7/32 inch diameter punches for the 1 mg tablets and 9/32 inch diameter punches for the 10 mg tablets. Additional strengths such as 0.5, 5, and 20 mg tablets are prepared using appropriate variations in the above formulation.

We claim:
1. A pharmaceutical composition in dosage unit form having β-adrenergic stimulant activity comprising a pharmaceutical carrier and an amount sufficient to produce β-adrenergic stimulant activity of a compound of the formula

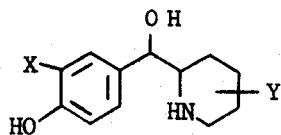

where
X is $(R)_2NCONH$, $RCONH$, $(R)_2N$, $R'OCONH$, or $R'SO_2CH_2$;
each R is hydrogen or $C_1$–$C_3$ alkyl;
R' is $C_1$–$C_3$ alkyl; and
Y is hydrogen or $C_1$–$C_6$ alkyl,
or a non-toxic pharmaceutically acceptable salt thereof.
2. A pharmaceutical composition as claimed in claim 1 where Y is hydrogen.
3. A pharmaceutical composition as claimed in claim 3 where X is $(R)_2NCONH$.
4. A pharmaceutical composition as claimed in claim 2 where X is RCONH.
5. A pharmaceutical composition as claimed in claim 2 where X is $(R)_2N$.
6. A pharmaceutical composition as claimed in claim 2 where X is R'OCONH.
7. A pharmaceutical composition as claimed in claim 2 where X is $R'SO_2CH_2$.
8. A pharmaceutical composition as claimed in claim 3 where R is hydrogen, the active medicament being the compound α-(4-hydroxy-3-ureidophenyl)-2-piperidylcarbinol.
9. A pharmaceutical composition as claimed in claim 5 where R is hydrogen, the active medicament being the compound α-(3-amino-4-hydroxyphenyl)-2-piperidylcarbinol.
10. A pharmaceutical composition as claimed in claim 7 where R' is methyl, the active medicament being the compound α-(4-hydroxy-3-methanesulfonylmethylphenyl)-2-piperidylcarbinol.

* * * * *